(12) United States Patent
Kaye et al.

(10) Patent No.: US 8,711,353 B2
(45) Date of Patent: Apr. 29, 2014

(54) FLUID-BORNE PARTICLE DETECTOR

(75) Inventors: Paul Henry Kaye, Herts (GB); Warren Roy Stanley, Herts (GB)

(73) Assignee: The Secretary of State for Defence (GB)

( * ) Notice: Subject to any disclaimer, the term of this patent is extended or adjusted under 35 U.S.C. 154(b) by 372 days.

(21) Appl. No.: 12/864,064

(22) PCT Filed: Jan. 22, 2009

(86) PCT No.: PCT/GB2009/000158
§ 371 (c)(1),
(2), (4) Date: Aug. 18, 2010

(87) PCT Pub. No.: WO2009/093017
PCT Pub. Date: Jul. 30, 2009

(65) Prior Publication Data
US 2010/0328665 A1      Dec. 30, 2010

(51) Int. Cl.
*G01N 21/00* (2006.01)

(52) U.S. Cl.
USPC ............. 356/342; 356/436; 356/336; 356/73; 250/575

(58) Field of Classification Search
USPC .................... 356/342, 436, 336, 73; 250/575
See application file for complete search history.

(56) References Cited

U.S. PATENT DOCUMENTS

| | | | |
|---|---|---|---|
| 5,767,967 A | 6/1998 | Yufa | |
| 5,895,922 A * | 4/1999 | Ho | 250/492.1 |
| 7,126,687 B2 * | 10/2006 | Hill et al. | 356/336 |
| 7,436,515 B2 * | 10/2008 | Kaye et al. | 356/436 |
| 7,920,261 B2 * | 4/2011 | Jeys et al. | 356/338 |
| 2004/0159799 A1 | 8/2004 | Saccomanno | |
| 2005/0243307 A1 | 11/2005 | Silcott et al. | |
| 2006/0050279 A1 * | 3/2006 | Kurozumi et al. | 356/436 |
| 2007/0013910 A1 | 1/2007 | Jiang et al. | |
| 2007/0285661 A1 * | 12/2007 | Saunders et al. | 356/336 |

FOREIGN PATENT DOCUMENTS

| | | |
|---|---|---|
| GB | 2311603 | 10/1997 |
| GB | 2434444 | 7/2007 |
| WO | WO-9317322 | 9/1993 |
| WO | WO-9859233 | 12/1998 |
| WO | WO-2005001436 | 1/2005 |
| WO | WO-2005029046 | 3/2005 |

OTHER PUBLICATIONS

Kaye, P. et al., "A dual-wavelength single particle aerosal fluorescence monitor,"Proceedings of SPIE, 2005, vol. 5990, pp. 59900N-1 through 59900N-12.

* cited by examiner

*Primary Examiner* — Tarifur Chowdhury
*Assistant Examiner* — Isiaka Akanbi
(74) *Attorney, Agent, or Firm* — Dean W. Russell; Kristin M. Crall; Kilpatrick Townsend & Stockton LLP

(57) ABSTRACT

There is disclosed improved apparatus and methods for detection of shape, size and intrinsic fluorescence properties of a fluid borne particle wherein the apparatus comprises a laser, two light sources, two detectors, and optionally a third detector. The apparatus is particularly suitable for detection of airborne biological particles.

11 Claims, 9 Drawing Sheets

FLUID-BORNE PARTICLE DETECTOR

CROSS REFERENCE TO RELATED APPLICATIONS

This application is the U.S. national phase of International Application No. PCT/GB2009/000158 filed on Jan. 22, 2009 and published in English on Jul. 30, 2009 as International Publication No. WO 2009/093017 A1, which application claims priority to Great Britain Patent Application No. 0801375.7 filed on Jan. 25, 2008, the contents of both of which are incorporated herein by reference.

This invention is concerned with improvements in apparatus and methods for detecting and classifying fluid borne particles, especially airborne particles, and is particularly concerned with detection of single biological particles.

In a world increasingly concerned with pollution, global warming and terrorism the requirement for reliable, accurate and sensitive techniques for detecting, and more importantly identifying airborne particles has never been more important. A significant amount of effort has been spent in developing and improving techniques and apparatus for achieving such detection over the years, but the requirement for more sensitive, compact, economical and cost-effective apparatus still exists.

Airborne particles include inter alia mineral dusts, combustion products and biological particles. In order to discriminate between airborne particles of different types methods have been developed which measure multiple parameters from individual particles, using means such as light scattering or fluorescence. International Patent Application PCT/GB2004002761 (Published as WO 2005/001436), incorporated in its entirety by reference herein, discloses apparatus for detecting fluid borne particles comprising a pair of coaxially opposed concave reflective surfaces having central apertures about a detection zone, two xenon light sources of differing wavelength band arranged to irradiate particles within the zone, and two opposed detectors either side of and substantially aligned with the reflective surfaces, arranged such that fluorescent light reflected from the concave reflective surfaces through the central aperture of the opposite concave reflective surface is received by a detector. The apparatus is capable of classifying particles in terms of their size (elastic scatter) and dual-wavelength intrinsic fluorescence properties. Detection of single particles using such an arrangement may be achieved by incorporation of a trigger to detect the presence of separate particles in the detection zone, such a trigger may be provided by a continuous wave diode laser such as described in Kaye P. H. et al Proceedings SPIE European Symposium Optics/Photonics in Security and Defence Bruges, September 2005, 59900 N1-N12. A timing sequence is then required to enable sequential illumination of a single particle by the two xenon light sources as the particle flows through the detection zone of the apparatus.

Apparatus disclosed in International Patent Application PCT/GB2004002761 was designed for analysis in outdoor environments and especially areas of military conflict whereby a biological threat may appear anywhere. For this purpose the apparatus was required to be of sufficiently low cost and small size so that it may be manufactured in large numbers for utilisation over a wide area of potential risk. Such an apparatus would also optimally be hand portable, require no or minimal reagents, be capable of unattended operation and continuous operation for approximately 48 hours. The apparatus also had to be sensitive and provide a rapid detection response.

The present invention generally aims to provide compact apparatus capable of sensitively detecting and classifying single particles through fluorescence and light scattering. The invention in particular aims to improve classification capability and compactness provided by apparatus disclosed in International Patent Application PCT/GB 2004002761.

Accordingly, in a first aspect, the present invention provides an apparatus for detection of a fluid borne particle comprising i. a pair of coaxially opposed concave reflective surfaces about a zone whereby flow means are provided for delivering a fluid flow comprising the fluid borne particle through the zone;

ii. a laser arranged to illuminate the fluid flow in the zone;

iii. a first and second detector wherein the first detector is arranged to detect scattered and/or emitted light of a first wavelength band emanating from the zone and the second detector is arranged to detect scattered and/or emitted light of a second wavelength band emanating from the zone;

iv. a first and second light source wherein the first source is arranged to illuminate the fluid flow in the zone with light of a third wavelength band and the second source is arranged to illuminate the fluid flow in the zone with light of a fourth wavelength band whereby the laser and the first and second light source are each arranged in a plane substantially orthogonal to the direction of the fluid flow provided for by the flow means.

Advantageously, the coaxially opposed concave reflective surfaces comprise central apertures such that light emanating from the zone, most likely produced through irradiation of the particle, is focussed by the concave reflective surfaces through the central aperture of the opposite concave reflective surface. The first and second detector are advantageously arranged to detect light focussed through the central aperture of the opposed concave reflective surfaces. Preferably, the axis linking the centre of the opposed concave reflective surfaces is substantially aligned with the axis linking the detectors. The axis linking the centre of the opposed concave reflective surfaces is also preferably substantially orthogonal to the axis of illumination from the laser. These features either singularly or combined facilitate efficient collection and detection of light scattered or emitted by particles within the zone of the apparatus.

The laser and the first and second light source are each arranged in a plane substantially orthogonal to the direction of the fluid flow provided for by the flow means to provide for optimal focussing of the first and second light sources onto a specific volume of the fluid flow that is illuminated by the laser. The laser illuminates a specific volume of the fluid which as a result of the laser being in a plane substantially orthogonal to the fluid flow appears as approximately a flat cylinder or disk shape. A light source also in a plane substantially orthogonal to the fluid flow will require the minimum width of light beam to illuminate the whole specific volume of the flat cylinder shape, and therefore be of optimal power for producing fluorescence and detection.

Embodiments of the first aspect of the invention may have the laser and the first and second light source situated such that the laser and first and second light sources are each in a plane vertically offset with respect to each other. Alternatively, the laser and the first and second light sources may be substantially in the same plane but the resulting light beams from the laser and the first and second light source may each be in a plane vertically offset with respect to each other. The resulting light beams from the laser and the first and second light source may be vertically offset to allow for movement of the particle under the influence of the fluid flow between triggering of the laser, the first light source and the second light source. Thus a particle illuminated and sensed by the light beam from the laser at a first position in the zone may be illuminated by the light beam from the first light source at a second position in the zone downstream of the first position, and may be illuminated by the light beam of the second light source at a third position in the zone downstream of the second position.

In a preferred embodiment however the laser and two light sources are substantially arranged in a single plane substantially orthogonal to the direction of the fluid flow provided for by the flow means. This provides amongst other advantages for a more compact apparatus. Furthermore, apparatus of the present invention having the laser and the two light sources substantially arranged in a single plane provides an increase in sensitivity of approximately six-fold over that of the apparatus disclosed in International Patent Application PCT/GB2004002761 and Kaye P. H. et al Proceedings SPIE European Symposium Optics/Photonics in Security and Defence Bruges, September 2005, 59900 N1-N12.

In a preferred embodiment the two detectors are each arranged in a plane substantially orthogonal to the direction of the fluid flow provided for by the flow means, and in a more preferred embodiment the two detectors are in the same plane as the laser and the first and second light source. Such an embodiment provides for a compact arrangement of features, and therefore more compact apparatus. Apparatus having the laser, the first and second light source, and the two detectors all in a single plane is in particular more compact, approximately half the volume, than apparatus disclosed in the cited prior art documents.

The first and second light source preferably comprise a xenon light source element and preferably a low pass filter between the light source and the zone to allow passage of a wavelength band in a selected range only.

The apparatus is particularly suitable for detecting an airborne particle, and especially a biological particle such as a bacterial cell, bacterial spore, bacterial cell fragment or a virus containing particle.

One use of the apparatus is the classification of biological particles through intrinsic fluorescent properties of molecules present within the particle. Two of the most useful molecules are tryptophan and nicotinamide adenine dinucleotide (NADH) which fluoresce upon irradiation with wavelengths of approximately 280 nm and 370 nm, respectively, resulting in fluorescence emission between about 300 to 400 nm for tryptophan and about 400 to 600 nm for NADH. Thus in one embodiment the third wavelength band may be shorter in wavelength than the first wavelength band and the second wavelength band, and/or the fourth wavelength band may be shorter in wavelength than the second wavelength band, and/or the fourth wavelength band may be within the first wavelength band.

In one embodiment, the first and second light sources are xenon lamps such as miniature xenon flash lamps which may be focussed down to a few $mm^2$ and deliver the necessary high UV fluence (approximately 200-300 $\mu J/sr/cm^2$) required to achieve an adequate fluorescence response from a biological particle in a 1 μs duration of illumination. The third wavelength band is preferably about 280 nm and the fourth wavelength band preferably about 370 nm, as these are wavelength bands suitable for exciting tryptophan (280 nm) and NADH (370 nm).

The first wavelength band and the second wavelength band may overlap, however preferably the first wavelength band and the second wavelength band are not overlapping. Overlapping wavelength bands may result in an increase of low-level background broadband fluorescence emanating from objects other than the particle itself, becoming manifest as noise incorporated in each measurement. Furthermore, and for substantially the same reasons, the first wavelength band and second wavelength band are relatively narrow in range. In one embodiment suitable for detecting intrinsic fluorescence from tryptophan and NADH the first wavelength band is approximately 300 to 400 nm and the second wavelength band is approximately 420 to 600 nm.

The laser preferably provides for a continuous wave laser beam to identify the presence of a single particle in the zone, and may for example be a 635 nm continuous wave diode laser.

The apparatus may further comprise a third detector for detecting forward scattered light as a result of illuminating the particle by the laser and/or the first or second light source. Such a detector is capable of providing an assessment or even identification of the shape of the particle, and therefore provides for improved apparatus over that disclosed in the cited prior art. The third detector may for example comprise a quadrant photomultiplier tube detector. The third detector may assess particle shape through analysis of azimuthal light scattering from the particle. In an embodiment of the apparatus wherein the second detector is capable of detecting back or side (elastic) scattered light the apparatus may further comprise feedback means between the second detector and the third detector such that the feedback means provides for accurate measurement and identification of particle size. The second detector may for example be capable of detecting back or side scattered light when the wavelength of the laser light beam is within the wavelength band of the second detector (the second wavelength band): scattered light resulting from illumination of a particle with the laser could therefore be detected at the second detector. The combination of two different detectors for recording size and shape measurement through light scattering is capable of reducing the effect of Mie oscillations in a sizing response curve and therefore is capable of providing a more reliable particle size measurement.

Preferably the apparatus further comprises a processor configured to operate the apparatus whereby triggering and/or timing of illumination from the laser and the first and second light sources are controlled. The processor may also be programmed to process light signals received at the first and second detector, and where applicable the third detector.

In a second aspect, the present invention provides a method for detection of a fluid borne particle comprising sequentially illuminating a fluid flow with a laser, a first light source and a second light source, whereby the laser illuminates a specific volume of the fluid flow and records the presence of the fluid borne particle and the first light source and the second light source illuminate the specific volume to elicit fluorescent signals from the particle which are detected by suitable means for light detection, whereby the laser, first light source and second light source are each arranged in a plane substantially orthogonal to the fluid flow.

It should be noted that in a fluid flow the specific volume, in which the presence of a fluid-borne particle is detected by the light beam from the laser, will move as a result of the flow of the fluid and thus the light beam from the first and/or second light source, or both may have to be focussed such as to compensate for this movement. For example, the laser and the first and second light source may be situated with respect to each other such that the laser and first and second light sources are vertically offset. Alternatively, the laser and the first and second light sources may be substantially in the same plane but the resulting light beams from the laser and the first and second light source may be vertically offset.

In a preferred embodiment the method utilises apparatus of the first aspect of the invention.

In a third aspect, the present invention provides a use of apparatus of the first aspect for detecting fluid-borne particles.

In a preferred embodiment, the fluid is air, and in a further preferred embodiment the particles are biological particles.

The present invention will now be described with reference to the following examples and drawings in which FIG. 1 is a drawing of one embodiment of the present application;

FIG. 2 is an image indicating the geometry of one aspect of the present invention wherein the fluid flow is substantially orthogonal to a plane comprising a laser, two light sources and three detectors;

FIG. 3 a) and b) are schematics comparing apparatus of the cited prior art (a) wherein illumination of particles is with a laser in a plane substantially orthogonal to the direction of the fluid flow but a xenon light source not in a plane substantially orthogonal to the direction of the fluid flow, and an embodiment of the present invention (b) wherein illumination of particles is with a laser and a xenon light source each in a plane substantially orthogonal to the direction of the fluid flow;

Figure 8:
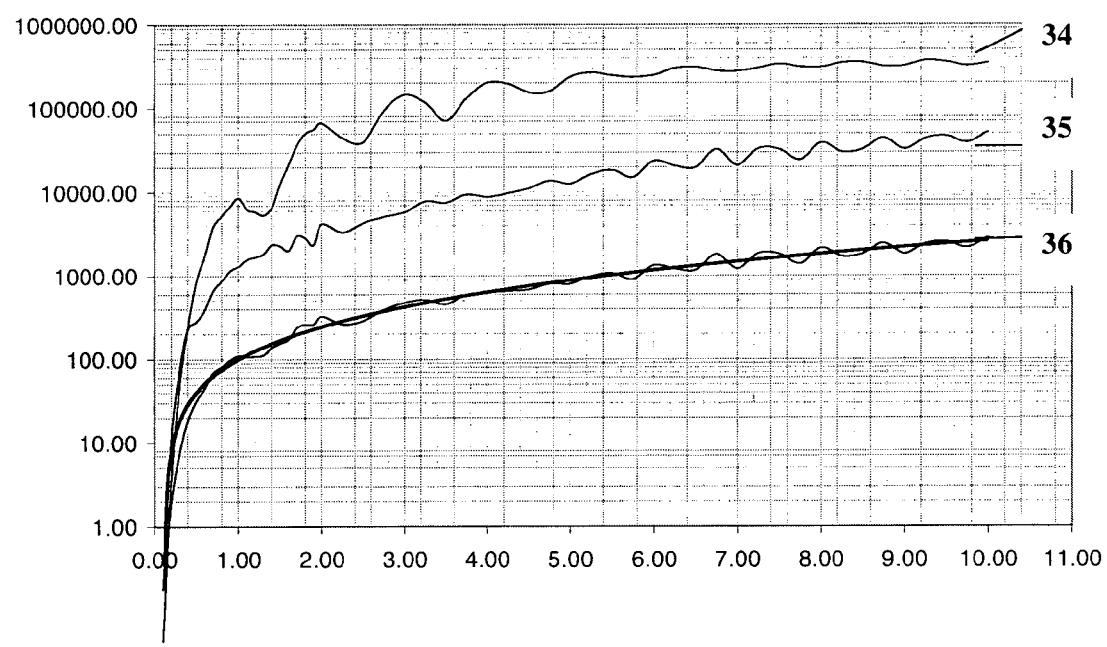
Figure 9:
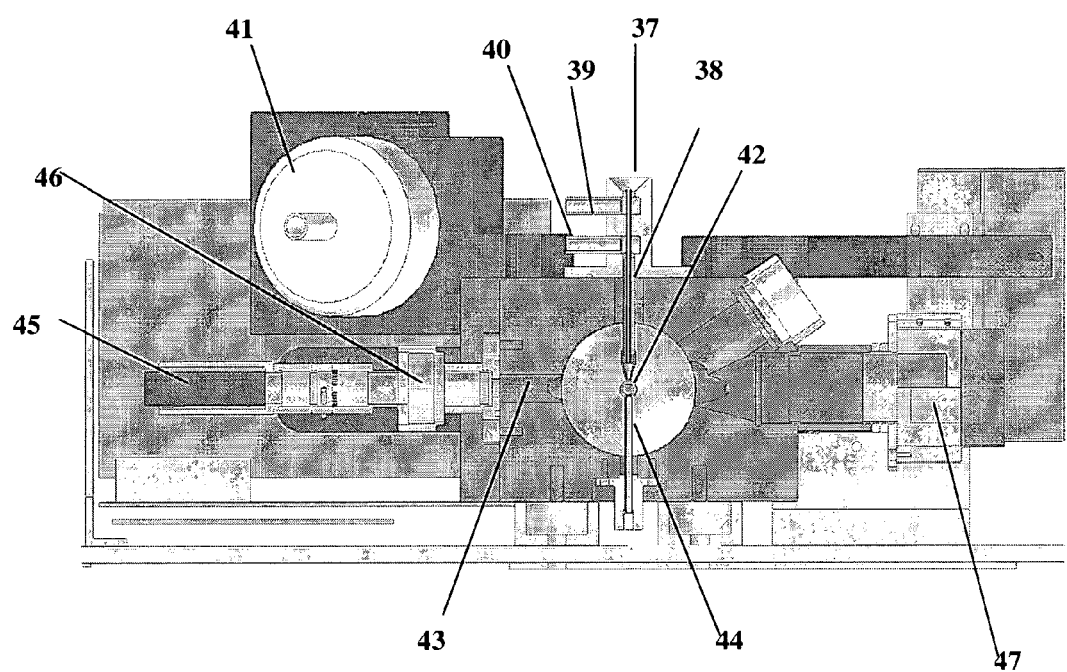

FIG. 8 is a graph of relative light flux (y axis) against particle diameter (x axis; μm), and shows the theoretical response for a quadrant photomultiplier tube detecting forward scattered light 34, a second photomultiplier tube detecting back or side scattered light 35, and a mathematical combination 36 of these two responses for identifying particle size; and FIG. 9 is a cross-sectional view of one embodiment of the apparatus of the present invention showing, in particular, features providing for an aerosol to be delivered to the detection zone.

EXAMPLES

Figure 1:
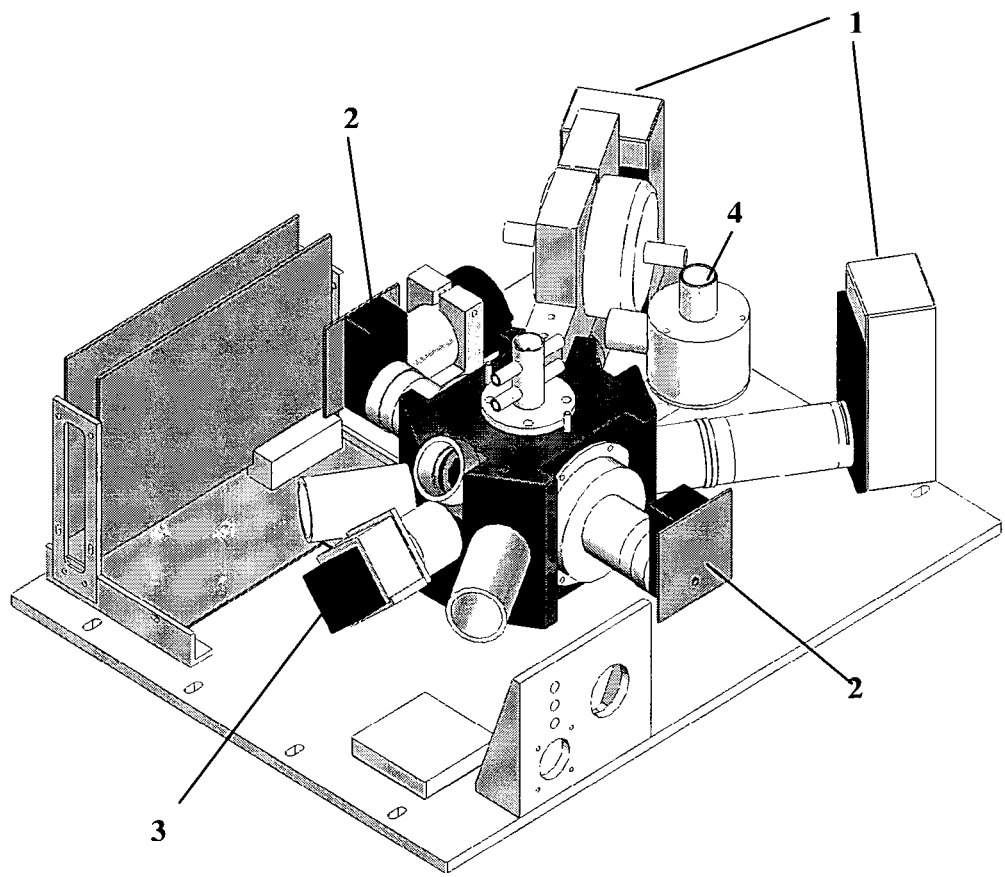

Referring now to FIG. 1, an embodiment of the present invention for measuring the size, shape and intrinsic fluorescence from individual particles comprises two xenon light sources 1, two detectors 2, a quadrant detector 3 and a laser (not visible in the figure) all in a single plane wherein the plane is substantially orthogonal to the fluid flow within the detection zone of the apparatus. An aerosol inlet 4 is also present for providing the fluid flow, i.e. the airflow. Wavebands of the two xenon light sources are 280 nm and 370 nm, and are selected to excite the biofluorophores tryptophan and NADH. One detector is arranged to record a wavelength band between approximately 300 and 400 nm, and the other detector a wavelength band between approximately 420 and 600 nm. The apparatus is in particular for detecting particle sizes between about 0.5 μm to 10 μm. Maximum throughput for a complete fluorescence measurement is 125 particles/second (limited by xenon recharge time), and corresponds to all particles for concentrations up to approximately $2 \times 10^4$/liter. This embodiment is half the size of apparatus disclosed in International Patent Application PCT/GB2004002761 and apparatus in Kaye P. H. et al Proceedings SPIE European Symposium Optics/Photonics in Security and Defence Bruges, September 2005, 59900 N1-N12, and has approximately a 6-fold improvement in fluorescence detection sensitivity. The xenon light sources may be arranged on the same side of the apparatus as the laser, as shown, or alternatively on the opposite side of the apparatus, but still in the same plane, as indicated in FIG. 2.

Figure 2:
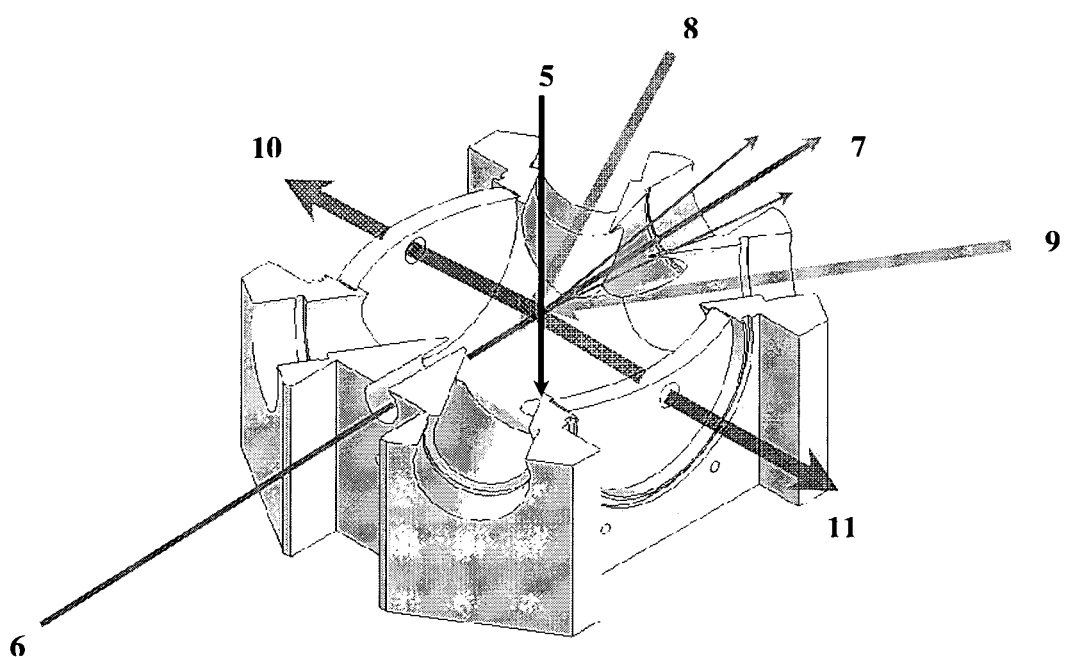

Referring now to FIG. 2, the geometry of an embodiment of the present invention provides for a fluid flow 5 substantially orthogonal to a plane comprising the laser light beam 6 providing forward scattered light 7 and the xenon light source beams 8 and 9 providing particle fluorescence 10 and 11. The shape of the central component of the apparatus (substantially elongated cylindrical) displayed in FIG. 2 is driven by the requirement to arrange all features around a particular zone, the detection zone of the apparatus, and to provide apparatus as compact as possible. In one embodiment of the invention the central component has dimensions of approximately height 80 mm, width 100 mm, and length 120 mm. The remaining dimensions of this component are driven by the requirement to fit specific components of the apparatus.

One embodiment of the apparatus of the present invention comprises the components listed in Table 1 arranged around the central component displayed in FIG. 2. This embodiment of the apparatus can be fitted into a container, or box, of dimensions 170 mm height, 300 mm wide and 380 mm long, and thus provides for a compact apparatus which is also hand portable.

TABLE 1

Component list for one embodiment of the present invention.

| Item | Item Description | Use | Supplier | order code | Quantity |
|---|---|---|---|---|---|
| Lenses | 60 mm fl DCX UV coated | xenon light sources | Edmund Optics | A46-294 | 4 |
|  | 25 mm fl DCX UV coated | first detector | Edmund Optics | A46-292 | 2 |
|  | 25 mm fl PCX Vis coated | second detector | Edmund Optics | A45-363 | 1 |
|  | 30 mm fl PCX Vis coated | second detector | Edmund Optics | A45-098 | 1 |

TABLE 1-continued

Component list for one embodiment of the present invention.

| Item | Item Description | Use | Supplier | Item order code | Quantity |
|---|---|---|---|---|---|
| | 50 mm fl 25 mm dia cyl | diode laser beam shaping | Edmund Optics | A46-017 | 1 |
| | lens 50 mm fl | third detector | Edmund Optics | A32-478 | 1 |
| | lens 75 mm fl | third detector | Edmund Optics | A32-480 | 1 |
| | Quaterwave plate | third detector | Melles Griot | 02WRM001 | 1 |
| Filters | Sem 280 filter | first xenon light source | Laser2000 (SEMrock) | FF01-280/20-25 | 2 |
| | Sem 304 filter | first detector | Laser2000 (SEMrock | FF01-300/LP-25 | 2 |
| | DUG11 filter | second xenon light source | HV Skan | DUG11 | 1 |
| | DUG11 filter | first detector | HV Skan | DUG11 | 1 |
| | UG11 | first detector | HV Skan | UG11 | 1 |
| | KV418 filter | second detector | HV Skan | KV418 | 1 |
| Mirrors | Edmund | visible reflection mirror | Edmund Optics | A43-469 | 2 |
| Lens tubes | Thor Iris diaphragms 25 mm | | ThorLabs | SM1D12 | 2 |
| | Thor lens tube | | ThorLabs | SM1L03 | 8 |
| | Thor lens tube | | ThorLabs | SM1L05 | 5 |
| | Thor lens tube | | ThorLabs | SM1L10 | 2 |
| | Thor lens tube | | ThorLabs | SM1L20 | 2 |
| | Thor lens tube | | ThorLabs | SM1L30 | 2 |
| | Thor linking pieces | | ThorLabs | SM1T2 | 5 |
| | Thor retaining ring | | ThorLabs | SM1RR | 20 |
| | Lens tube couplers | | ThorLabs | SM05T2 | 2 |
| | Lens tube adaptors | | ThorLabs | SM1A6 | 1 |
| | Lens tube endcaps | | ThorLabs | SM1CP2 | 2 |
| Optoelectronics | 623 nm 12 mW laser | diode laser | Photonic products | 401-PM | 1 |
| | PMT modules | first and second detector | Hamamatsu | H6779 | 2 |
| | Xenon light source | first and second light source | Hamamatsu | L9455-01 | 2 |
| | 4-anode PMT | third detector | Hamamatsu | R5900U-01-M4 | 1 |
| | Socket for 4-anode PMT | third detector | Hamamatsu | E7083 | 1 |
| | HT supply for PMT 12 V | third detector | Hamamatsu | C4900-01 | 1 |
| | Red LED 12 V | Power and pump indicator | Onecall | 882-781 | 2 |
| | Blue LED 12 V | particle detect | Onecall | 882-823 | 1 |
| | Silicon photodiodes BPX65 | power monitors | RS | 304-346 | 2 |
| Electrical | DC-DC converter | power board | RS | 473-5801 | 1 |
| | Panel mount receptacle, pin contacts | power connector | Onecall | 391-1317 | 1 |

TABLE 1-continued

Component list for one embodiment of the present invention.

| Item | Item Description | Use | Supplier | order code | Quantity |
|---|---|---|---|---|---|
| | Straight plug-pin contacts - solder | power connector | Onecall | 391-1688 | 1 |
| | Plug backshell | power connector | Onecall | 391-2127 | 1 |
| | 1 m USB cable type A-B | internal connector | Onecall | 107-6669 | 1 |
| | IP68 B-type USB panel mount connector | USB port | Onecall | 966-7750 | 1 |
| | USBBuccaneer cable IP68 B-type to standard | External USB connector | Onecall | 999-7407 | 1 |
| Mechanical | Barbed connector/kit | tubing connector | Cole Palmer | KH-31514-02 | 1 |
| | Barbed elbow/Tee Y connector kit | tubing connector | Cole Palmer | KH-31514-14 | 1 |
| | Airlite 3 lpm diaphragm pump | air movement | SKC Ltd | | 1 |
| | air filters | air filtration | Fisher Scientific | FDP-780-030Q | 2 |

Figure 3:
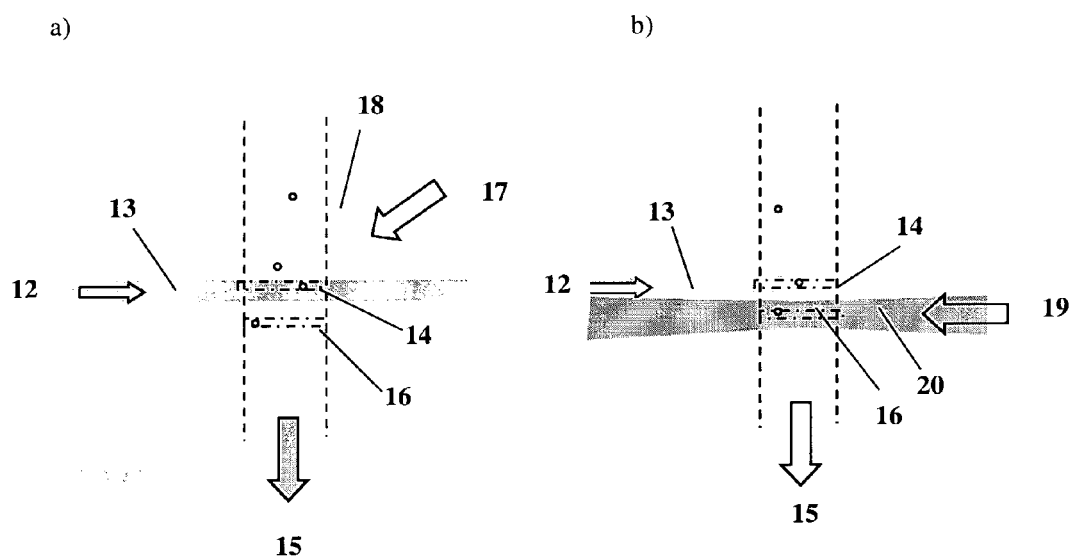

Referring now to FIG. 3a, apparatus disclosed in the cited prior art comprises a laser 12 providing a laser beam 13 to illuminate a specific volume 14 of a fluid flow 15. The specific volume moves with the fluid flow to a second position, volume 16, at which point a xenon light source 17 illuminates volume 16 to generate fluorescence from a particle initially present in specific volume 14. The xenon light source 17 provides a light beam 18 at an angle (approximately 30 to 45 degrees) to volume 16 and thus the width of light beam 18 is broad to accommodate for this arrangement: volume 16 must be as uniformly illuminated as possible. Referring now to FIG. 3b, apparatus of the present invention also comprises a laser 12 providing a laser beam 13 to illuminate a specific volume 14 of a fluid flow 15. However, a xenon light source 19 is arranged to produce a light beam 20 in the same horizontal plane as laser beam 13 which allows the width of the laser beam to be significantly less broad, and therefore more tightly focussed, whilst retaining full and complete irradiation of volume 16. The effect achieved by this arrangement of features is that a higher intensity of UV light illuminates each particle resulting in an enhanced fluorescence response.

Figure 4:
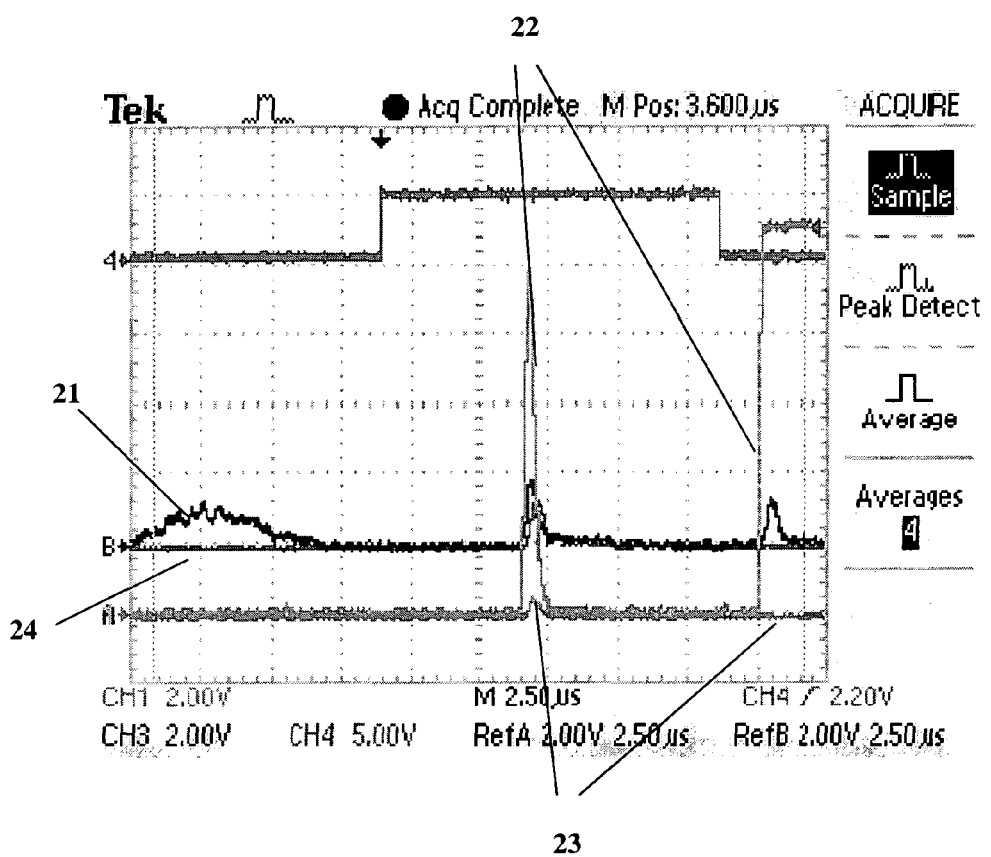
FIG. 4 is a graph representing light intensity recorded at a first detector and a second detector against time for one embodiment of the present invention.

Now referring to FIG. 4, results produced with the embodiment of FIG. 1, trace 21 is the response of the second detector following illumination of the zone, i.e. the detection zone, of the apparatus with a laser, a first xenon light source and a second xenon light source. The relatively long 10 μs signal produced in trace 21 is due to the particle passing through the laser beam and scattering light. The much shorter fluorescence pulses (~1 μs) appear due to firing of the two xenon light sources. Trace 22 is the response of the first detector, which upon irradiation with the first xenon light source (280 nm) records a signal corresponding to particle fluorescence in the wavelength band of 300 to 400 nm, and upon irradiation with the second xenon light source (370 nm) records elastically scattered light from the particle, as the wavelength of the second light source falls within the wavelength band of the first detector, which saturates the detector. Trace 23 just visible beneath trace 22 shows the response of the first detector to firing of the two xenon light sources in the absence of a particle. Trace 24 is the response of the second detector to firing of the two xenon light sources in the absence of a particle. Ideally this should result in zero detected signal, however because of imperfect filters and low levels of fluorescence within the scattering chamber itself, a measurable signal is detected. This is one of the factors that ultimately limits the sensitivity of the instrument. This 'background' fluorescence signal is approximately 1/20 of the signal recorded from a 3 μm polystyrene calibration particle. For comparison, in the apparatus disclosed in International Patent Application PCT/GB2004002761 and apparatus disclosed in Kaye P. H. et al Proceedings SPIE European Symposium Optics/Photonics in Security and Defence Bruges, September 2005, 59900 N1-N12 the recorded background signal is approximately 1/3 of the signal recorded for a 3 mm polystyrene calibration particle, and thus the embodiment of FIG. 1 possesses a 6-fold improvement in sensitivity. The improvement is due to lower levels of stray UV light in the chamber and higher levels of UV fluence on the particle which are both as a result of horizontal alignment of the xenon light sources and the laser, with each feature being present in a plane substantially orthogonal to the direction of the fluid flow, thus allowing the xenon light sources to be focused more tightly.

The timing sequence for triggering of the laser and the two xenon light sources in order to irradiate (illuminate) a single particle is calculated based on the rate of air flow through the apparatus. A description of the process performed within one embodiment of the apparatus (such as that illustrated in FIG. 1), together with the triggering sequence, is as follows:

1. As a particle passes through the 635 nm laser light beam light is scattered in all directions, with forward scattered light falling on the quadrant photomultiplier tube, which provides data for particle detection and assessment of particle shape. Light scattered at a range of angles around +/−90 degrees falls on the two concave mirrors and is reflected through the aperture in the opposing mirror to one of the detectors. The first detector is not capable of detecting the scattered light as due to the specific filter mounted to the detector it is only capable of detecting wavelengths of light between 300 and 400 nm. The second detector however does register this scattered light producing a signal proportional to the amount of light (see broad signal in trace 21 of FIG. 4). This signal is used together with the forward scattered signal (not shown in FIG. 4) at the quadrant photomultiplier tube to determine particle size.

2. Approximately 10 μs after the particle is detected, by scattered light recorded at the second detector, the first xenon light source (280 nm) is triggered to fire. During this 10 μs period, the particle will have moved approximately 300 μm and will be below the level of the laser beam. The fluorescence from the particle is collected by both the first and second detectors (see signals in trace 21 and 22 in FIG. 4).

3. A further 10 μs later, the second xenon light source (370 nm) fires, and again the fluorescence excited in the particle by this longer wavelength UV is collected by the first and second detectors (see trace 21 and 22 in FIG. 4). It should be noted that as the second light source has a wavelength band (370 nm) within that of the first detector wavelength band (300 to 400 nm) the detector in fact records the light intensity of the light source scattered elastically by the particle, and since this is generally several orders of magnitude larger than the fluorescence typically expected from a particle, the signal recorded at this detector (see trace 22 of FIG. 4) saturates and is of no material value in assessing the particle.

The xenon light sources are then recharged, which takes approximately 5 ms, before the sequence can be repeated. The time for recharging combined with the thermal limit of 125 flashes/second for the xenon light sources limits the number of particles that can be measured to approximately 125 particles per second. Any particles which pass through the laser beam while the xenon light sources are recharging are detected and counted, however no fluorescence measurements are made. Furthermore, because the particle moves approximately 500 μm during each measurement cycle, the two xenon light sources and the first and second detectors may be arranged each in a plane below that of the laser beam to improve the efficiency of capture of the fluorescence light from the particle.

Figure 5:
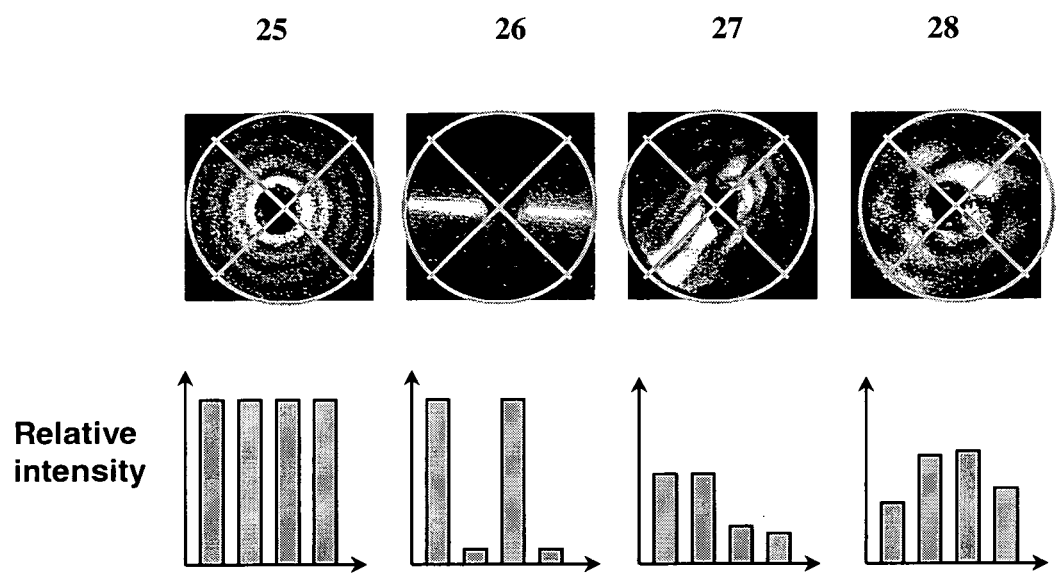
FIG. 5 is a diagram indicating light scattering patterns recorded with a quadrant detector for particles of different shape.
Figure 6:
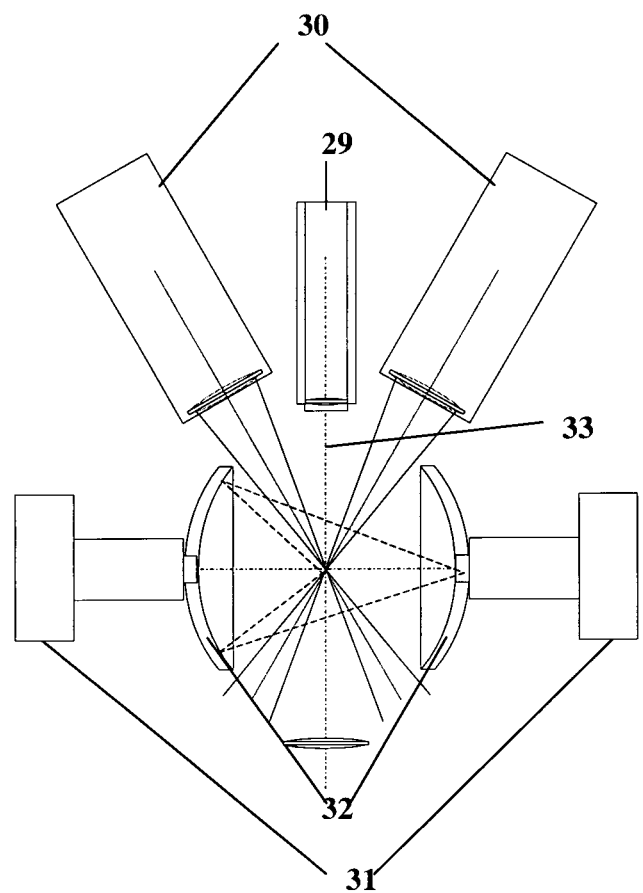
FIG. 6 is a diagram indicating the spatial arrangement of components of one embodiment of the present invention in a horizontal plane.
Figure 7:
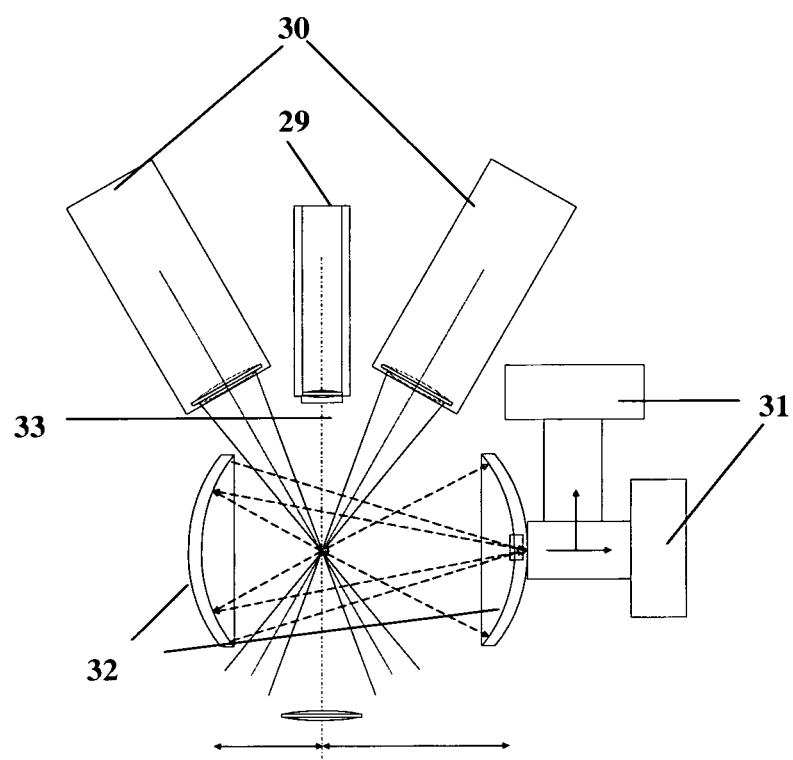
FIG. 7 is a diagram indicating the spatial arrangement of components of another embodiment of the present invention in a horizontal plane.

To reduce the occurrence of false positive results and to improve particle size measurement the particle shape is assessed through azimuthal distribution of scattered light around the axis of the light beam. For this, a quadrant photomultiplier tube detector is a feature of the apparatus. Elongated particles such as fibres or rod-shaped bacilli tend to align with their long axis parallel to the airflow axis. The scattering pattern from the particle is then characteristic of the shape of the particle and its alignment. This shape measurement allows the apparatus to differentiate between particles with similar fluorescence characteristics such as unburnt fuel droplets from that of *Bacillus globigii* spores: fuel droplets are reported as spherical, the spores are not. Now referring to FIG. 5, the response of the four photomultiplier tube channels enables characterisation and identification of a droplet 25 (spherical), a fibre 26 (where its vertical alignment leads to predominantly horizontal scattering), a flake-like particle 27, and an irregular shaped particle 28 (no specific geometry). The values recorded in each of the four channels enables computation of a single Asymmetry Factor (Af) for the particle, based on the root-mean-square of the variation in intensity about the laser beam axis (azimuth). Af is scaled to give 0 for a perfect sphere and 100 for a long fibrous particle. In practice, because of limitations in signal-to-noise in the four channels, spherical particles do not give 0 but normally a small value, typically <5.

Assessment of particle size using the embodiment of FIG. 1 is performed by combining the forward light scattered response recorded at the quadrant photomultiplier tube detector with the side light scattered response recorded at the second detector which provides for a more accurate size measurement than either response alone. The response curve resulting from the output of the quadrant photomultiplier tube taken alone is not monotonic but shows Mie oscillations at various points, which means that conversion of the output to a particle size value cannot be done without ambiguity. Similarly, the scatter signal output recorded at the second detector is proportional to the particle size but not monotonically. It too has Mie oscillations in the response curve, but these occur at different particle sizes to those in the quadrant photomultiplier tube response curves. Thus by combining the output of the two detectors the unwanted affects of the ambiguities in sizing caused by the Mie oscillations can be minimised (see FIG. 8).

Now having regard to FIG. 6, the arrangement of the components (laser 29, xenon light sources 30, the two detectors 31, and the two concave glass minors 32 containing central apertures) in one embodiment of the apparatus is essentially symmetrical, in a horizontal plane, about the laser beam axis 33 with one minor, one detector and one xenon light source on each side of the laser beam 33. In this embodiment the separation of the minor surfaces at their common axis is 3/2× focal length of the minors so that light from the detection zone of the apparatus is reflected from one minor and back through the aperture in the second mirror and onto the detector, as illustrated in FIG. 6. The angular position of the xenon light sources in the horizontal plane is unimportant, but is governed by mechanical considerations of fitting the xenon optics into the space provided ensuring that the beam of light from each xenon light source exits from the zone, i.e. the space between the mirrors, without the light beam being incident on either mirror. A mirror focal length of 25 mm is utilised in this embodiment of the apparatus to ensure that the minor separation is sufficient to allow the two xenon sources and the laser optics to all fit in the horizontal plane, and illuminate the zone of the apparatus. The mirrors in this embodiment are of a longer focal length than the mirrors in the apparatus disclosed in Kaye P. H. et al. Proceedings SPIE European Symposium Optics/Photonics in Security and Defence Bruges, September 2005, 59900 N1-N12 (focal length of 17.5 mm) in which the two xenon light sources and the laser are in the same vertical plane, which is not substantially orthogonal to the direction of the airflow, and thus the mirrors are capable of being closer together without interfering with the light beams. The result of this is that light collection by each mirror in this embodiment of the invention is slightly less than that of the apparatus in the cited prior art, however this disadvantage is more than offset by the advantage of having the two xenon light sources both in the horizontal plane, wherein they may be focussed more tightly onto the specific volume of the fluid flow.

Now having regard to FIG. 7, it is not essential to have a detector either side of the laser beam 33, as both detectors 31 may be present on a single side of the laser beam 33 as shown. Here the mirrors 32 are separated by 3× focal length of the mirrors. Light from a particle scattered or emitted towards the right hand mirror is reflected back through the zone onto the left hand mirror and then reflected back through the aperture in the right hand mirror. Light scattered or emitted towards the left mirror is also reflected through the aperture in the right hand mirror. The collected light can then impinge on a dichroic mirror at 45° to reflect light in one wavelength band (300 to 400 nm) to one detector whilst light in a second wavelength band (400 to 600 nm) is transmitted to the second detector.

Now having regard to FIG. 8, the theoretical light flux responses (y axis) at the quadrant detector 34 (forward scattered light) and the second photomultiplier tube detector 35 (back/side scattered light) were calculated for increasing particle sizes (x axis) using Mie theory, assuming all particles to be spherical. The responses 34 and 35 show that scatter signals measured by these sensors can be used to gain an impression of particle size. However, both curves show undulations (Mie oscillations) which means that sizing of a particle based on a single detector response can be ambiguous (i.e. a horizontal line may intersect the line at more than one point, and thus more than one particle size is possible). To minimise the problem the responses 34 and 35 were combined such that response 34 is dominant for particle sizes up to 3 mm and response 35, the weaker of the two but less prone to Mie oscillations, is dominant for larger particle sizes. To achieve this response 35 was squared to increase its magnitude with respect to response 34, and further mathematically modified to improve the match between the two signals. This entailed changing the exponent of response 35 from 2 to 2.1, and dividing the result by 1000. Response 36 shows the two signals combined. The plot is actually the square root of the combination, i.e. the square root of Response 34 plus Response $35^{2.1}/1000$. The square root allows a good fit of a second order rather than a third order polynomial to response 36, which exhibits much smaller Mie oscillations. The polynomial equation $y=16.779x^2+95.563x-11.966$ is then used in software to convert the combined scatter signals into a single particle size approximation.

Now having regard to FIG. 9, a cross section of one embodiment of the apparatus along the laser beam axis shows features for enabling an aerosol to be flowed to the detection zone of the apparatus, and thereby illuminated with a laser beam 43. Ambient air is drawn into aerosol inlet 37 by the air pump at a rate of 2,115 ml/min. Some 211 ml of the airflow (10%) continues to flow down the central sample delivery tube 38, of 1.65 mm internal diameter. The remainder of the airflow is extracted through a side tube 39 and is reintroduced at another side tube 40 as a particle-free sheath flow after passing through a HEPA filter 41. The two airflows join as a laminar flow at the end of the sample delivery tube and are focused to a narrower total diameter of 1 mm by a tapered inlet nozzle 42. The sample flow is constrained to a vertical column of ~0.6 mm diameter as it passes through the laser beam 43 5 mm below the tip of nozzle 42. The air is then vented through Vent tube 44.

The laser beam 43 is provided by a continuous wave 12 mW diode laser module 45 at 635 nm wavelength. The output beam from the laser is linearly polarised and must be rendered circularly polarised in order to ensure that the particle scattering pattern received by the quadrant photomultiplier detector 47 is not affected by polarisation effects which could impair characterisation of particle shape from the detector data. The beam then passes through a cylindrical lens 46 of 75 mm focal length such that, at the intersection of the beam with the sample airflow, the beam is approximately 150 μm deep. This intersection, referred to as the specific volume is disc shaped of dimensions 0.6 mm diameter and 150 μm thick. A particle in this specific volume will scatter light to the quadrant PMT detector 47 which is positioned such that the centre of the quadrant lies on the beam axis and the lines separating the quadrants being at 45° to the vertical.

The invention claimed is:

1. An apparatus for detection of a fluid borne particle and for measuring the particle size, comprising:
   i. a pair of coaxially opposed concave reflective surfaces separated by three times focal length of the concave reflective surfaces about a zone whereby flow means are provided for delivering a fluid flow comprising the fluid borne particle through the zone;
   ii. a laser arranged to illuminate the fluid flow in the zone;
   iii. a first and second detector wherein the first detector is arranged to detect scattered and/or emitted light of a first wavelength band emanating from the zone, the second detector is arranged to detect scattered and/or emitted light of a second wavelength band emanating from the zone and the second detector is capable of detecting back or side scattered light;
   iv. a first and second light source wherein the first source is arranged to illuminate the zone with light of a third wavelength band and the second source is arranged to illuminate the zone with light of a fourth wavelength band; and
   v. a third detector arranged to detect forward scattered light as a result of illuminating the particle by the laser and/or the first or second light source to provide an assessment or identification of particle shape
   whereby the laser and the first and second light source are each arranged in a plane substantially orthogonal to the direction of the fluid flow provided for by the flow means, the second detector and the third detector are capable of recording size measurement through light scattering, and
   the apparatus further comprises a feedback system between the second detector and the third detector that combines output from the second and third detector to reduce the effect of Mie oscillations in a sizing response curve in order to provide accurate measurement and identification of a single particle size.

2. An apparatus according to claim 1 wherein the first and second detectors are arranged in a plane substantially orthogonal to the direction of the fluid flow provided for by the flow means.

3. An apparatus according to claim 1 wherein the laser and the first and second light source are substantially arranged in a single plane substantially orthogonal to the direction of the fluid flow provided for by the flow means.

4. An apparatus according to claim 3 wherein the first and second detectors are substantially arranged in the same plane as the laser and the first and second light source.

5. An apparatus according to claim 1 wherein the third wavelength band is shorter in wavelength than the first wavelength band and the second wavelength band.

6. An apparatus according to claim 1 wherein the third detector is arranged in the same plane as the laser and the first and second light sources.

7. An apparatus according to claim 1 wherein the first wavelength band is 300 to 400 nm.

8. An apparatus according to claim 1 wherein the second wavelength band is 420 to 600 nm.

9. An apparatus according to claim 1 wherein the third wavelength band is 280 nm and the fourth wavelength band is 370 nm.

10. An apparatus according to claim 1 wherein the third detector is a quadrant photomultiplier tube detector.

11. Use of the apparatus according to claim 1 for detecting fluid borne particles.

* * * * *

UNITED STATES PATENT AND TRADEMARK OFFICE
Certificate

Patent No. 8,711,353 B2                                                                Patented: April 29, 2014

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Paul Henry Kaye, Herts (GB); Warren Roy Stanley, Herts (GB); and Emma Virginia Jane Foot, Salisbury (GB).

Signed and Sealed this Twenty-fifth Day of November 2014.

TARIFUR R. CHOWDHURY
*Supervisory Patent Examiner*
Art Unit 2886
Technology Center 2800